United States Patent
Boyd et al.

(10) Patent No.: US 6,206,923 B1
(45) Date of Patent: Mar. 27, 2001

(54) FLEXIBLE IMPLANT USING PARTIALLY DEMINERALIZED BONE

(75) Inventors: Lawrence M. Boyd, Memphis; John A. Pafford, Germantown, both of TN (US)

(73) Assignee: SDGI Holdings, Inc., Wilmington, DE (US)

(*) Notice: Subject to any disclaimer, the term of this patent is extended or adjusted under 35 U.S.C. 154(b) by 0 days.

(21) Appl. No.: 09/227,976

(22) Filed: Jan. 8, 1999

(51) Int. Cl.[7] .................................. A61F 2/44; A61F 2/28
(52) U.S. Cl. ..................................... 623/17.11; 623/16.11; 623/23.63; 623/919
(58) Field of Search ................ 623/17.11, 17.16, 623/23.63, 23.71, 23.74, 908, 919, 923, 16.11

(56) References Cited

U.S. PATENT DOCUMENTS

| | | | |
|---|---|---|---|
| 4,627,853 | 12/1986 | Campbell et al. | 623/16 |
| 4,678,470 | 7/1987 | Nashef et al. | 623/16 |
| 4,743,259 | 5/1988 | Bolander et al. | 623/16 |
| 4,932,973 | 6/1990 | Gendler et al. | 623/16 |
| 5,053,049 | 10/1991 | Campbell | 623/16 |
| 5,108,438 | 4/1992 | Stone | 623/17 |
| 5,112,354 | 5/1992 | Sires | 623/16 |
| 5,139,505 | 8/1992 | Palmieri | 606/154 |
| 5,147,402 | 9/1992 | Bohler et al. | 623/16 |
| 5,417,975 | 5/1995 | Lussi et al. | 424/423 |
| 5,425,769 | 6/1995 | Snyders, Jr. | 623/16 |
| 5,439,684 | 8/1995 | Prewett et al. | 424/422 |
| 5,455,231 | 10/1995 | Constantz | 514/21 |
| 5,464,439 | 11/1995 | Gendler | 623/16 |
| 5,507,813 | 4/1996 | Dowd et al. | 623/16 |
| 5,510,396 | 4/1996 | Prewett et al. | 523/113 |
| 5,562,736 * | 10/1996 | Ray et al. | 623/17.16 |
| 5,585,116 | 12/1996 | Boniface et al. | 424/549 |
| 5,645,591 | 7/1997 | Kuberasampath et al. | 623/16 |
| 5,735,902 | 4/1998 | Li et al. | 623/18 |
| 6,039,761 | 3/2000 | Li et al. | 623/17 |
| 6,090,998 * | 7/2000 | Grooms et al. | 623/16.11 |

FOREIGN PATENT DOCUMENTS

| | | | |
|---|---|---|---|
| WO 98/48739 | 11/1998 | (WO) | A61F/2/44 |
| 99/09914 | 3/1999 | (WO) | |
| 99/21515 | 5/1999 | (WO) | |
| 99/38453 | 8/1999 | (WO) | |
| WO 99/42062 | 8/1999 | (WO) | A61F/2/44 |

OTHER PUBLICATIONS

University of Florida Tissue Bank, Inc. "MD–I™ and MD–II™ Custom Machined Cortical Dowels".

Sofamor Danek—The Spine Specialist "Surgical Technique Using Bone Dowel Instrumentation For Posterior Approach" ©1996.

University of Florida Tissue Bank, Inc. "MD–III™ Threaded Cortical Dowel—Design Rationale and Surgical Technique".

Gen Sci—Regeneration Sciences Inc.—3 Internet pages, Nov. 16, 1999, www.gensci.bc.ca/products.htm.

* cited by examiner

Primary Examiner—David H. Willse
Assistant Examiner—Choon P. Koh
(74) Attorney, Agent, or Firm—Woodard, Emhardt, Naughton, Moriarty & McNett

(57) ABSTRACT

Implantable devices useful for creating bony fusion particularly in intervertebral spinal fusion. The device is formed of bone and has an at least partially demineralized portion between two rigid bone portions creating an area of flexibility. In one application, the area of flexibility may be used to move the device between a reduced size insertion configuration and an expanded implanted configuration. In another use, the area of flexibility may be useful to dampen shock applied to the implant. A method is also disclosed for making the implants and inserting the implants into an intervertebral disc space to promote interbody fusion.

11 Claims, 7 Drawing Sheets

FLEXIBLE IMPLANT USING PARTIALLY DEMINERALIZED BONE

BACKGROUND OF THE INVENTION

The present invention relates to implantable fusion devices and methods for their use. More particularly, the present invention relates to interbody fusion devices formed of bone that may be utilized in spinal fusions.

A variety of interbody fusion implants are available for spinal fusion procedures. These implants have been manufactured of various materials including steel, titanium, composites, allograft, xenograft or other biocompatible materials. These implants may be inserted using fixed protective tubes to protect surrounding neurological and vascular structures or through an unprotected open procedure. One limitation on the size of a device inserted into the disc space is the size of the opening through surrounding tissue that is available to gain access to the disc space. From a posterior approach to the spine, the dura and nerve roots must be mobilized to gain access to the disc space. Similarly, from an anterior approach, the aorta and vena cava must be mobilized to gain access to the disc space. Such mobilization is often limited by the anatomical structures, thus resulting in a relatively small access site in comparison to the size of the disc space. Removal of additional ligaments and bone to enlarge an entrance to the disc space may de-stabilize and weaken the joint between two adjacent vertebra. Moreover, excessive retraction of vessels and neural structures to create a large access opening may result in damage to these tissues. Thus, prior procedures have been limited to placing a first device passable through the available opening on one side of the spine and mobilizing the tissue or vessels to place another similar implant on the opposite side of the spine. Each implant being limited in size by the available access site.

In response, expandable implants have been developed from biocompatible materials such as titanium and composites. These devices rely on hinges or selective deformation of the implant material to permit expansion after they are positioned in the disc space. While such devices have a reduced insertion configuration and an expanded spacing configuration, the materials utilized to form the implants are synthetic and will not incorporate into adjacent bony tissues. While bone offers much improved incorporation, the inherent brittle nature of bone resulting from a high mineral content, particularly load-bearing cortical bone, severely limits its potential deformation. Typically, for example, cortical bone consists of approximately 70% mineral content and 30% non-mineral matter. Of this non-mineral matter, approximately 95% is type I collagen, with the balance being cellular matter and non-collagenous proteins.

Bone grafts, in conjunction with other load-bearing implants, have commonly been used in a fixed shape, pulverized, or as pliable demineralized bone. One form of a pliable bone graft is a demineralized bone material typically in the form of a sponge or putty having very little structural integrity. While a demineralized bone segment may retain properties suitable to support bone ingrowth, the structural properties of the bone are altered by removal of its mineral content. Thus, such bone sponges and putties may not typically be used in load-bearing applications.

Therefore, there remains a need for a strong bone implant having an area of flexibility.

SUMMARY OF THE INVENTION

In one aspect, the present invention provides a flexible bone implant. The bone implant of the present invention comprises a first bone portion, a second bone portion, and a flexible bone portion joining the first and second bone portions. The intermediate flexible bone portion permits movement of the first bone portion in relation to the second bone portion. In a preferred embodiment, the movement of the first and second bone portions would be between a reduced size insertion configuration and an expanded configuration suitable for maintaining two bony structures in a spaced relation and permitting bone ingrowth, if desired. Optionally, the movement between the first and second bone portions may be utilized as an elastic damper when the device is positioned between adjacent bony structures.

In accordance with another aspect of the invention, the bone implant comprises a bone segment having at least one partially demineralized area creating a flexible segment of the demineralized bone segment. In one embodiment, an opposite portion of the cortical femoral ring segment is severed such that the ring segment may be expanded once it has been inserted into an intervertebral disc space. In yet another embodiment, the device includes at least two partially demineralized bone portions on substantially opposing portions of the bone segment. In this configuration, the substantially rigid portions are placed in contact with the load bearing surfaces between two adjacent bony structures such that the flexible portions perform an elastic function, allowing more normal motion or to better load bone adjacent the disc space.

In yet a further aspect of the present invention, there is provided a method for the preparation of a bone implant. The method includes providing a rigid bone segment and delineating an intermediate portion of that segment. The central portion is then at least partially demineralized to create a flexible segment between two adjacent sections of bone. The method of at least partially demineralizing a segment of bone between two adjacent rigid bone segments may be repeated as often as necessary to create the desired structure for implantation.

The present invention further contemplates a method of inserting a device formed in accordance with the present invention. Specifically, the method includes providing an insertion tube and an implant formed of bone having a first and second portions joined by a flexible central portion. The insertion tube is positioned adjacent a disc space formed by adjoining vertebrae. The first and second portions of the bone implant are then positioned into a reduced size configuration for insertion into the insertion tube. The implant is then inserted into the tube and advanced until it is positioned in the disc space. Once the implant is in the desired position, the first and second portions are moved with respect to one another by flexing of the flexible portion into an expanded implantation configuration. In a preferred embodiment of the insertion method, bone ingrowth material is placed between the first and second portions to encourage further bone ingrowth into and around the fusion devices.

These and other objects of the present invention will be apparent to those skilled in the art based on the following descriptions of the preferred embodiment of the present invention.

DESCRIPTION OF THE PREFERRED EMBODIMENTS

Figure 1:
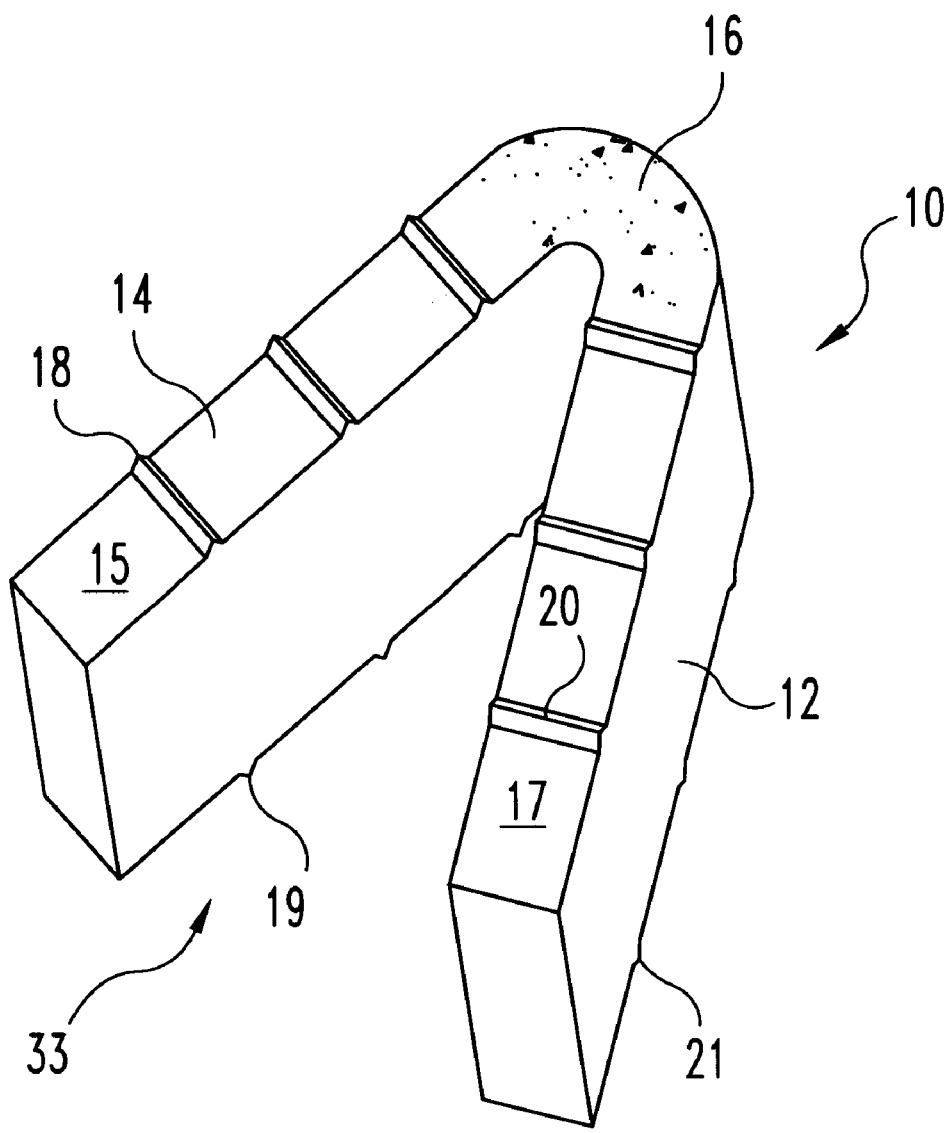
FIG. 1 is perspective view of an implant according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Referring now to FIG. 1, there is shown an implant according to a preferred embodiment of the present invention. Although implants according to the present invention may have many uses, the embodiment shown in FIG. 1 is particularly adapted for promoting interbody fusion in the spine. Specifically, FIG. 1 illustrates a bone implant 10 having a first substantially rigid portion 12 and a second substantially rigid portion 14. The first and second rigid portions 12 and 14 are joined by intermediate portion 16. Intermediate portion 16 has been at least partially demineralized to create an area of flexibility in the bone implant. Preferably, an area of intermediate portion 16 has been completely demineralized to provide maximum flexibility. The flexibility created by demineralization of intermediate portion 16 permits rigid portions 12 and 14 to be moved with respect to each other. The advantages of this feature will be further described herein.

Bone portion 12 includes bone engagement ridges 20 defined on upper bearing surface 17 with an identical set of ridges 21 defined on the bottom-bearing surface (not shown). In a similar manner, bone portion 14 includes bone engaging ridges 18 defined on upper bearing surface 15 and identical ridges 19 defined on the bottom-bearing surface (not shown). It will be understood that while ridges have been shown in a preferred embodiment, it is contemplated that there are a variety of structures, which could provide a surface for effective engagement with the vertebral bodies to limit expulsion from the disc space.

The rigid bone portions 12 and 14 are adapted to provide structural support between the respective upper and lower bearing surfaces. Specifically, the bone implant may be selected from donor bone having sufficient resistance to compression between the upper and lower surfaces to find application in the intended environment. The pair of rigid bone portions cooperate to provide support for spacing between adjacent vertebra. While the preferred embodiments of the implants according to the present invention have been shown with two rigid bone portions, it is contemplated that further rigid bone portions may be interconnected by flexible bone areas to offer further implant shapes.

Figure 2:
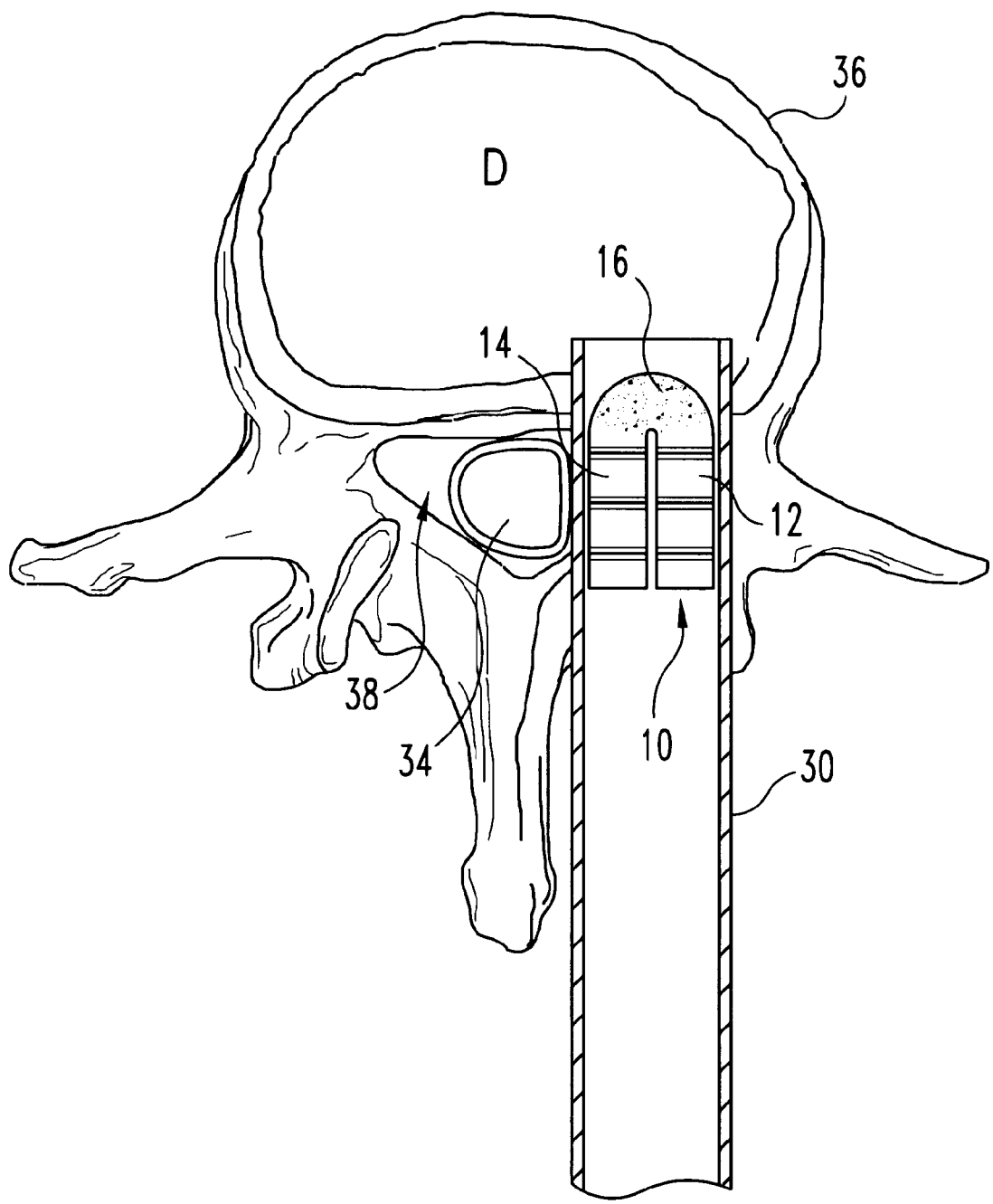
FIG. 2 is a top view of the implant in its insertion configuration.
Figure 3:
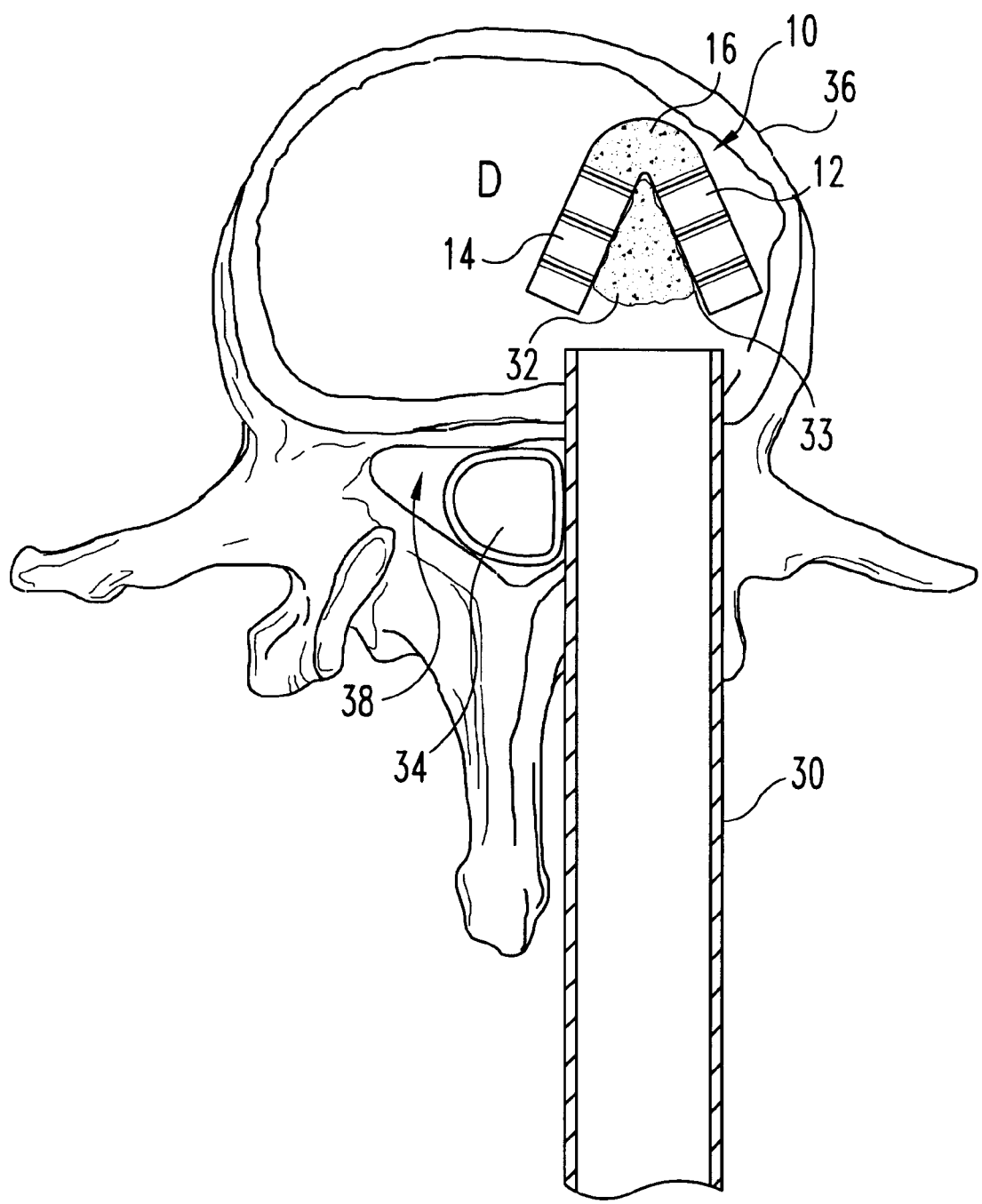
FIG. 3 is a top view of the implant in its expanded implanted condition.
Figure 4:
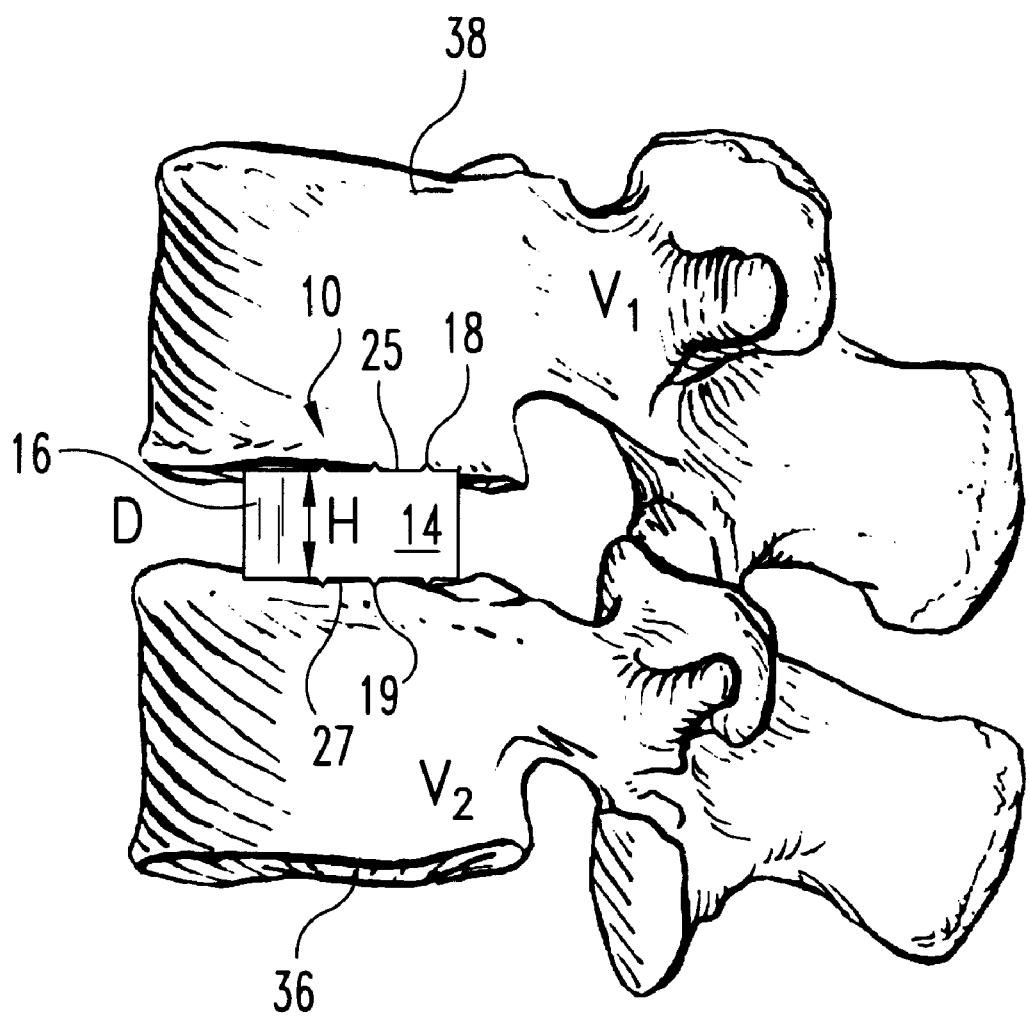
FIG. 4 is a side view of an implant according to the present invention inserted between two adjacent vertebra.

Referring now to FIGS. 2–4, there is shown a method of inserting a device according to the present invention for interbody fusion between adjacent vertebral bodies. Specifically referring to FIG. 2, implant 10 is shown in its reduced size insertion configuration with first portion 12 positioned substantially adjacent second portion 14. As shown in FIG. 2, it is contemplated that the rigid portions may be positioned in substantially parallel alignment. However, in some applications, this amount of flexibility in intermediate portion 16 may not be necessary. In a preferred embodiment, the implant is constrained in the insertion configuration within insertion tube 30.

Access to the disc space between adjacent vertebra is achieved as known in the art. Although access may be achieved from any direction without deviating from the invention, for the purpose of illustration and without limitation, FIGS. 2 and 3 illustrate access via a posterior approach. Once access is achieved, a protective sleeve may be positioned adjacent the disc space and the disc space distracted if necessary. Implant 10 is moved to the insertion configuration with the longitudinal extent of bone portions 12 and 14 in substantial parallel alignment. The implant, in the reduced size configuration, is positioned in protective sleeve 30 and advanced toward the disc space D. It will be understood that while implant 10 may have a much greater size after placement, dura 34 need only be retracted within cavity 38 enough to allow passage of protective sleeve 30 and the reduced size implant.

Implant 10 is advanced through protective sleeve 30 by use of a pushing device (not shown) until it exits protective sleeve 30 into the disc space D (FIGS. 3 and 4). Once in disc space D, the device either expands by release of an elastic deformation formed in the central portion 16 or a separate instrument (not shown) may be inserted between first portion 12 and second portion 14 to urge movement between the respective portions to manipulate the device into the expanded spacing configuration shown in FIG. 3. Expansion of the device creates an implant having greater stability to the intervertebral space via a broader support area and less tendency to topple over in the disc space. Further cavity 33 between portions 12 and 14 provides an area to receive material to promote bony incorporation and fusion. Once implant 10 has been properly positioned, bone growth promoting material 32 may be positioned between first portion 12 and second portion 14 to encourage bone growth into and through implant 10. Although not illustrated, it will be understood that typically a second implant will be placed in disc space D to provide further stability.

As shown more clearly in FIG. 4, implant 10 has a height H which is substantially equal to the height of disc space D formed between vertebra 36 and vertebra 38. It will understood by those skilled in the art that in the preferred embodiment illustrated herein, the height H is substantially constant from the insertion shown in FIG. 3 to the expanded configuration shown in FIG. 4. Furthermore, while a uniform height implant is shown in FIG. 2, it will be understood that implant 10 may have a tapering height such that the implant could be utilized for establishing or maintaining the proper lordotic curvature in the spine. With reference to rigid bone portion 14, upper bearing surface 25 engages and supports upper vertebral body 38 while lower bearing surface 27 engages and supports the implant on lower vertebral body 36. Rigids 18 and 19 engage the surface of vertebral bodies 38 and 36, respectively, to resist expulsion. Rigid bone portion 14, in conjunction with rigid bone portion 12 having similar engagement with the vertebrae, has sufficient rigid and structural integrity to substantially maintain height H and to withstand normal forces applied to the spinal column. Flexible area 16 need not have such structural requirements, although, preferably, it assists in the implant stability by maintaining the connection between the two support walls.

Flexible bone implant 10 provides the desirable features of being formed of a highly successful bone fusion material, i.e. natural bone, with the advantages of having a reduced size insertion configuration and an expanded spacing configuration. Thus, while the implant maintains the desired height of disc space distraction, the width of the implant opposite central portion 16 is readily expandable from the insertion configuration of FIG. 2 to the expanded configuration of FIG. 3. This feature permits insertion through a smaller access site and increases implant stability in the disc space.

Figure 5:
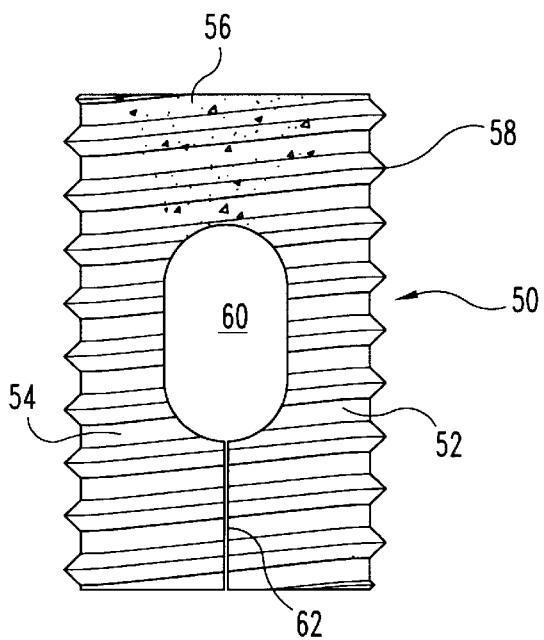
FIG. 5 is a top view of an alternative embodiment of the present invention.
Figure 6:
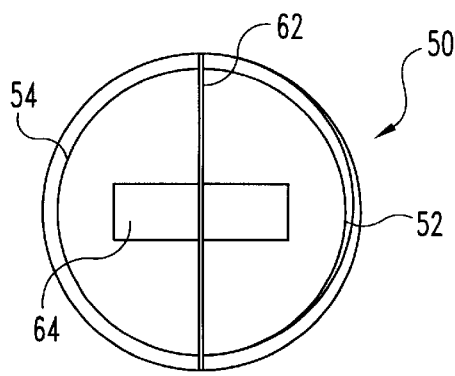
FIG. 6 is an end view of the embodiment of FIG. 5.
Figure 7:
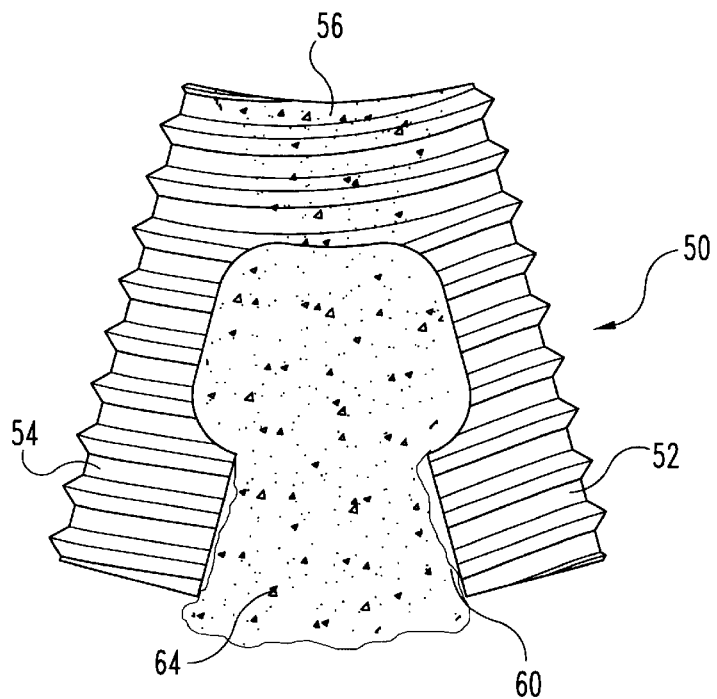
FIG. 7 is a top view of the implant of FIG. 5 in an expanded configuration.

Referring now to FIGS. 5 through 7, there is shown a further embodiment of an implant according to the present invention. FIG. 5 shows a threaded cortical bone dowel 50 modified in accordance with the present invention. Bone dowel 50 includes a thread 58 for engaging adjacent vertebra to advance the implant in a controlled manner and to resist expulsion. Implant 50 has a recessed slot 64 for engaging a driving tool adapted to rotate the device. In accordance with the invention, threaded bone dowel 50 is divided into a first side wall 52 and second side wall 54 separated by flexible area 56 and slot 62. As described further herein, flexible area 56 is created by at least partial demineralization of the bone in this area of the implant. Each of the first and second side walls 52 and 54 include upper and lower bearing surfaces. Threaded dowel 50 further includes a central opening 60. This opening may be created by the natural medullary canal of a diaphyseal bone or by removal of a cancellous portion of a donor bone, although this depends on the configuration of the donor bone.

In the configuration of FIG. 5, the device may be inserted through an insertion tube or other device into a disc space as previously described. Once positioned with opening 60 adjacent the upper and lower vertebral bodies, first side wall 52 and second side wall 54 are urged away from each other with the implant flexing at flexible portion 56. The implant 50 is shown in its expanded condition in FIG. 7. Once the desired expansion has been created, bone growth promoting material 64 may be inserted into the interior area 60 between first side wall 52 and second side wall 54. The side walls provide structured support to maintain the disc space height. As shown in FIGS. 5 through 7, bone implant 50 has a reduced-size insertion configuration and an expanded spacing configuration.

Figure 8:
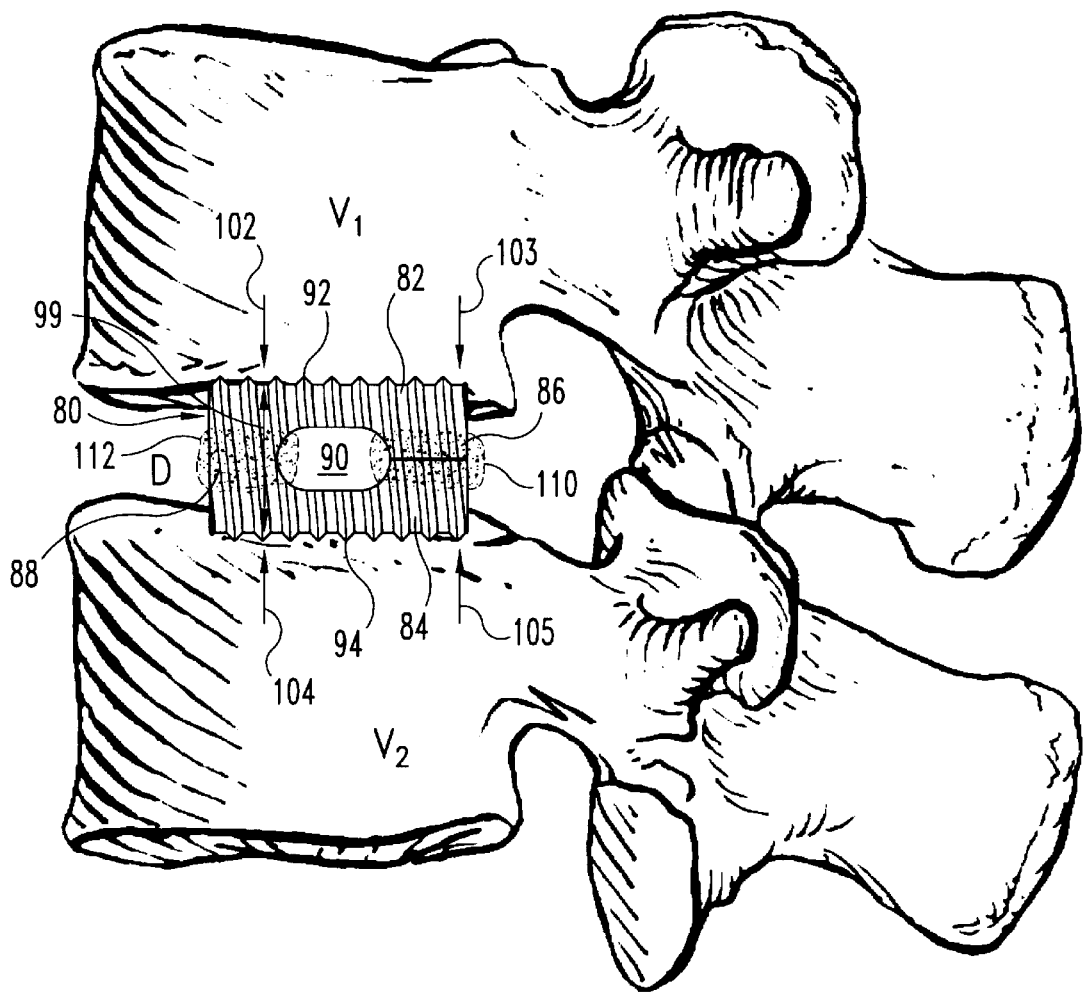
FIG. 8 is a side view of yet a further embodiment according to the present invention disposed between two adjacent vertebra.

Referring to FIG. 8, in still a further embodiment of the present invention, a threaded, cylindrical bone dowel has been modified in accordance with the present invention. Specifically, bone implant 80 has been modified to include at least two areas 86 and 88 of reduced mineral content, providing a degree of flexibility in the implant. Demineralized sections 86 and 88 are disposed between rigid portions 82 and 84. Thus, sudden changes in forces applied to rigid portions 82 or 84 may be dampened by the intervening flexible areas. Referring to FIG. 8, such a device is implanted in disc space 94 between vertebral body V1 and vertebral body V2 with rigid portions 92 and 94 positioned adjacent vertebral bodies V1 and V2, respectively. It will be understood that as force is applied to vertebral bodies V1 and V2, there will be a tendency for the implant to flex at demineralized areas 86 and 88 to provide a degree of flexibility in the implant and to provide physiologic loading environment. Specifically, compressive forces represented by arrows 102, 103, 104 and 105 may be more normally transferred by flexing of flexible portions 86 and 88 to positions 110 and 112, respectively. Such devices may have application in both fusion (normal loading) and arthroplasty (normal motion).

Figure 9:
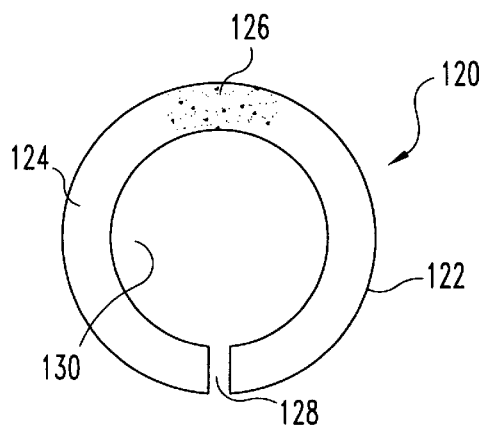
FIG. 9 is a top view of a ring-shaped bone segment prepared in accordance with another aspect of the present invention.

Referring to FIG. 9, there is shown yet a further aspect of the present invention. Donor bone 120 is a substantially ring-shaped bone segment having an internal cavity 30, such as a femoral ring. A slot 128 is formed in ring 120. Opposite slot 128, portion 126 is treated to remove at least a portion of the bone minerals. This creates an area of flexibility at portion 126. Thus, the bone is divided into side walls 122 and 124, separated by slot 128 and flexible portion 126. As previously described, the bone graft may be expanded after insertion by movement of side wall 124 away from side wall 122.

Figure 10A:
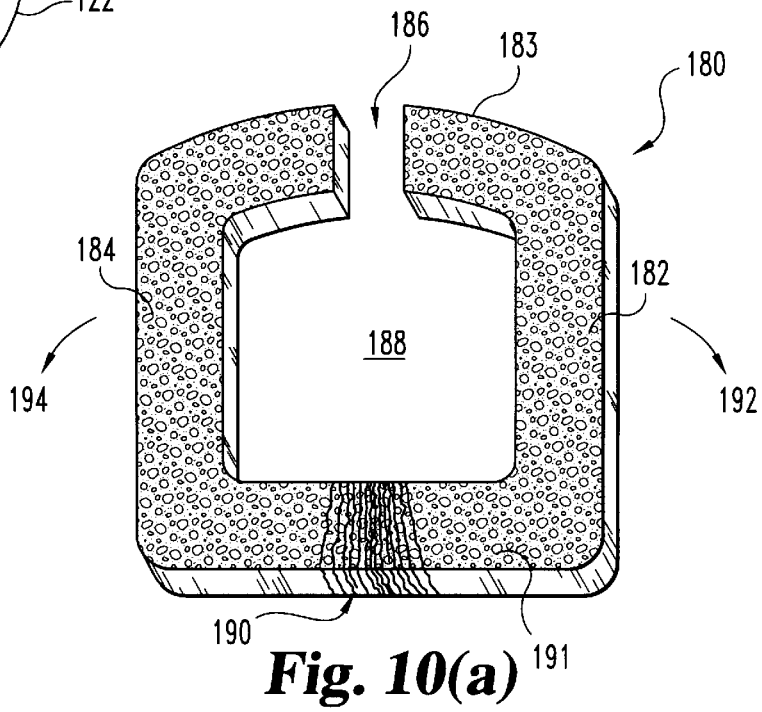
FIG. 10(a) is a top view of an alternative embodiment according to the present invention.
Figure 10B:
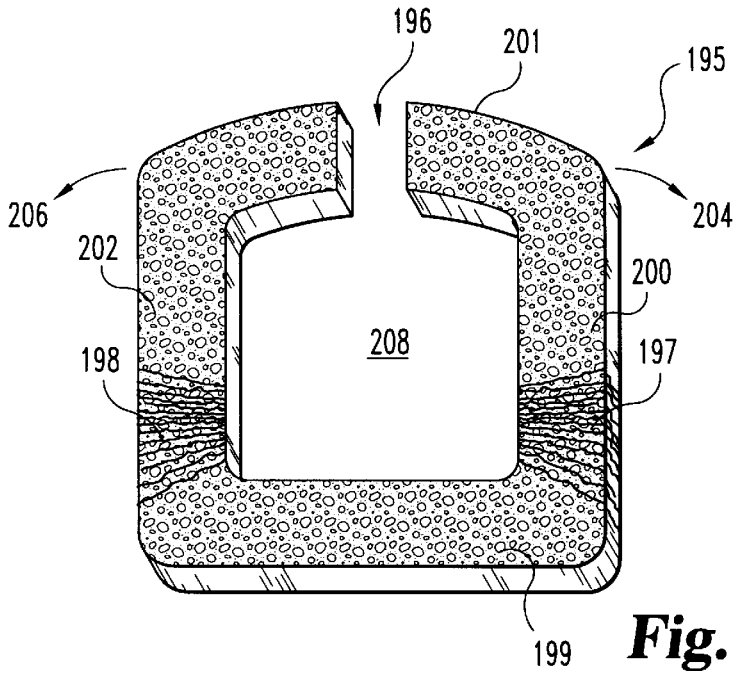
FIG. 10(b) is a modified embodiment of FIG. 10(a).

Referring now to FIG. 10(*a*), there is shown an alternative embodiment according to the present invention. Spacer 180 is a Smith-Robinson type bone graft that is typically used in the cervical region of the spine. Spacer 180 includes an internal cavity 188 defined by walls 182, 183, 184 and 191. Cavity 188 is suitable for receiving bone graft material to promote fusion between adjacent vertebrae. To provide for expansion, an opening 186 in wall 183 is created and an opposing flexible hinge area 190 is created in wall 191 by at least partial demineralization. In this manner, walls 182 and 184 may be moved in the direction of arrows 192 and 194, respectively, to expand the implant after insertion between adjacent vertebrae. It will be understood that wall 191 will be at least partially deformed during the expansion process.

FIG. 10(*b*) shows a modified embodiment of the implant of FIG. 10(*a*). In FIG. 10(*b*), spacer 195 has an internal chamber 208 defined by walls 199, 200, 201, and 202. Wall 201 includes an opening 196 formed there through. Flexible areas of bone are created by at least partial demineralization at hinge areas 197 and 198 on walls 200 and 202, respectively, adjacent the connection to wall 199. Walls 200 and 202 may be moved in the direction of arrows 204 and 206 to permit expansion of spacer 195. The use of dual hinge areas on the implant permits precise placement of wall 199 in the disc space and permits the expansion to take place laterally without the location of a portion of wall 199 being altered during expansion.

In addition to the above described embodiments, the present invention may have further uses. Specifically, but without limitation, one such may be to reform donor bone segments to conform more closely to spaces needing implants. In some cases, donor bone segments may have shapes incompatible with the shape of the implantation site. These bone segments may have flexible areas to reform the bone graft to more closely match its intended use. Such segments may have one or more flexible areas such that the overall shape of the donor bone segment may be modified by flexing at the flexible segments. This may preserve much of the load bearing strength of the implants. This use of the present invention may increase the potentially useable portions of the limited supply of donor bone. Full utilization of donor bone and alternative graft shapes is more fully disclosed in U.S. patent application Ser. No. 09/181,353 filed Oct. 29, 1998, entitled IMPACTED BONE IMPLANTS AND INSTRUMENTATION, incorporated herein by reference.

Creation of the demineralized portion of the bone will now be described. The processing involves the use of donor bone with processing in a clean room environment within a bone processing facility. Such donor bone may include allograft from human sources or xenograft from animal sources. Further, it is contemplated that as technology advances in the area of bone processing, the donor bone may be generated in the manufacturing process, either by bone growth or by a processing of constituent components of bone to create artificial materials having properties very similar to bone. More specifically, while any available allogenic or xenogenic bone stock may be utilized for the procedure, cortical bone is conventionally preferred for spinal fusion for its structural properties, although cortical cancellous or cancellous bone may be used depending upon the particular requirements for the implantable device.

In further processing, the connective tissues are removed and the bone is cleaned, rinsed, and defatted using a solvent such as ethanol or hydrogen peroxide. The bone is then machined or otherwise shaped using conventional techniques to create its final shape, such as a wedge, dowel, or other shape. An intermediate portion of the bone is delineated as needing an increased degree of flexibility. Demineralization takes place solely at the location requiring the flexible capability. Penetration of the demineralization fluid into the bone adjacent the desired area of flexibility may be controlled by hydrostatic pressure thereby limiting the area of demineralization. The amount of mineral removed from the bone may be adjusted to create the desired amount of flexibility. This demineralization conventionally uses an organic acid such as hydrochloric, nitric, or citric acid. Preferably, the demineralization solution comprises 0.1 to 1.0 N HCl, most preferably 0.3 N HCl. If a xenograft is used, known techniques on the utilization of organic solvents to inactivate bone proteins and reduce antigenecity may be applied at this point. Additionally, the use of glutaraldehyde may take place in order to further cross-line the collagen structure following removal of the mineral portion. Once the device has been machined and partially demineralized, it may be stored prior to insertion.

Although the above-described processing is disclosed herein as a preferred embodiment, it is contemplated that other suitable processes may be used.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An implant for promoting fusion between adjacent upper and lower vertebral bodies, comprising:
   a first bone portion;
   a second bone portion, and
   a flexible portion joining said first bone portion and said second bone portion, said flexible portion permitting movement of said first bone portion in relation to said second bone portion, wherein said first bone portion includes;
      an upper bearing surface for engaging said upper vertebra and a lower bearing surface for engaging said lower vertebra separated by a first height, and said second bone portion includes an upper bearing surface for engaging said upper vertebra and a lower bearing surface for engaging said lower vertebra separated by a second height, said first and second heights adapted to maintain spacing between adjacent upper and lower vertebral bodies.

2. The implant of claim 1, wherein said flexible portion is at least partially demineralized bone.

3. The implant of claim 2, wherein said flexible portion includes an area of completely demineralized bone.

4. The implant of claim 1, wherein said first height and said second height are substantially equal.

5. The implant of claim 1, wherein each of said upper and lower bearing surfaces includes a bone engaging surface to inhibit expulsion from a disc space between two adjacent vertebra.

6. The implant of claim 1, wherein said first and second bone portions have corresponding tapered bearing, surfaces to provide an implant having a spacing height gradually increasing from a first end to an opposite second end, wherein said implant is adapted for use in maintaining lordosis.

7. The implant of claim 1, wherein said first bone portion, said second bone portion, and said flexible portion are formed of a single bone segment.

8. An implant, comprising:
   a bone segment having a cortical bone portion extending between a first bearing surface and a second bearing, surface, said portion being at least partially demineralized to create a flexible segment wherein said bone segment is a ring shaped, and said bone segment includes a cut opposite said flexible segment, said cut dividing said bone segment into a first load bearing, portion extending between said cut and said flexible segment and an opposite second load bearing portion extending between said cut and said flexible segment.

9. A spinal fusion implant adapted for insertion into the space between adjacent first and second vertebral bodies, comprising:
   a first bone portion having a first bearing surface for engaging a first vertebral body;
   a second bone portion having a second bearing surface for engaging a second vertebral body;
   a proximal end and an opposite distal end;
   a first flexible portion disposed adjacent said proximal end and a second flexible portion, spaced from said first flexible portion, disposed adjacent to said distal end; and
   said flexible portions permitting, movement between said first bone portion and said second bone portion.

10. The implant of claim 9, wherein said first bearing surface and said second bearing surface includes cooperating thread patterns permitting threaded insertion of the implant into the space between the first and second vertebral bodies.

11. The implant of claim 9, wherein said implant is formed of a single segment of bone.

* * * * *